(12) United States Patent
Pedicini

(10) Patent No.: US 10,381,696 B2
(45) Date of Patent: *Aug. 13, 2019

(54) BATTERY ENCLOSURE FOR STERILIZEABLE SURGICAL TOOLS HAVING THERMAL INSULATION

(71) Applicant: DePuy Synthes Products, Inc., Raynham, MA (US)

(72) Inventor: Christopher Pedicini, Franklin, TN (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/009,723

(22) Filed: Jan. 28, 2016

(65) Prior Publication Data

US 2016/0218404 A1 Jul. 28, 2016

Related U.S. Application Data

(60) Provisional application No. 62/108,749, filed on Jan. 28, 2015.

(51) Int. Cl.
*H01M 10/658* (2014.01)
*H01M 2/10* (2006.01)
(Continued)

(52) U.S. Cl.
CPC ........... *H01M 10/658* (2015.04); *A61B 17/00* (2013.01); *A61B 17/1628* (2013.01);
(Continued)

(58) Field of Classification Search
None
See application file for complete search history.

(56) References Cited

U.S. PATENT DOCUMENTS 5,652,500 A * 7/1997 Kadouchi ........... H01M 10/443
320/150
6,756,766 B2 6/2004 Miller
(Continued)

FOREIGN PATENT DOCUMENTS

DE 103 19 350 A1 11/2004
JP 6-283217 A 10/1994
(Continued)

OTHER PUBLICATIONS

Kimura et al. (JP 2006-218228 A, machine translation).*
Abe et al. (JP H06-283217, machine translation).*
International Search Report and Written Opinion dated Nov. 2, 2016 in PCT/US2016/015380.
(Continued)

*Primary Examiner* — Wojciech Haske

(57) ABSTRACT

A battery pack assembly or enclosure comprises one or more batteries having an electrochemical cell and an enclosure having at least an outer wall configured to create a sealed volume of space substantially around the batteries. An atmosphere of the volume of space comprises gas having a thermal conductivity less than 0.018 watts per meter per degree Celsius. This atmosphere of gas provides an insulative layer between the outer wall of the enclosure and the batteries. With this insulative layer, the battery pack assembly can be subjected to autoclaving without damaging the batteries. The battery pack assembly can be used to power surgical tools or other devices that are subjected to autoclaving.

19 Claims, 4 Drawing Sheets

(51) Int. Cl.
*H01M 10/48* (2006.01)
*H01M 10/623* (2014.01)
*H01M 10/659* (2014.01)
*A61B 90/00* (2016.01)
*A61B 17/16* (2006.01)
*H01M 10/651* (2014.01)
*H01M 10/613* (2014.01)
*A61B 17/00* (2006.01)

(52) U.S. Cl.
CPC ........... *A61B 90/08* (2016.02); *H01M 2/1022* (2013.01); *H01M 2/1094* (2013.01); *H01M 10/482* (2013.01); *H01M 10/486* (2013.01); *H01M 10/613* (2015.04); *H01M 10/623* (2015.04); *H01M 10/651* (2015.04); *H01M 10/659* (2015.04); *A61B 2017/00734* (2013.01); *A61B 2090/0813* (2016.02); *H01M 2220/30* (2013.01)

(56) References Cited

U.S. PATENT DOCUMENTS

| | | |
|---|---|---|
| 8,486,560 B2 | 7/2013 | Tartaglia |
| 2005/0096661 A1 | 5/2005 | Farrow et al. |
| 2007/0264485 A1 | 11/2007 | Stepanian et al. |
| 2018/0013184 A1 | 1/2018 | Pedicini |

FOREIGN PATENT DOCUMENTS

| | | |
|---|---|---|
| JP | 7-226230 A | 8/1995 |
| JP | 2006-218225 A | 8/2006 |
| JP | 2006-218228 A | 8/2006 |
| JP | 2007-319769 A | 12/2007 |
| JP | 2010-040362 A | 2/2010 |

OTHER PUBLICATIONS

Examination Report for European Application No. 16712549.1 dated May 10, 2019.

* cited by examiner

BATTERY ENCLOSURE FOR STERILIZEABLE SURGICAL TOOLS HAVING THERMAL INSULATION

RELATED APPLICATION

This application claims the benefit, under 35 U.S.C. § 119(e), to provisional application Ser. No. 62/108,749.

BACKGROUND

The present disclosure relates to the thermal insulation of a battery enclosure and, for example, to an insulation of an enclosure containing battery cells that is exposed to high temperatures during operation.

Battery powered tools have provided increased convenience and productivity to medical professionals in surgical settings. These surgical tools and their associated batteries are sterilized before utilization, such as in the sterile field of an operating room. Battery powered surgical tools are typically designed to withstand the temperatures associated with an autoclave cycle for sterilizing a surgical tool or instrument. These temperatures may reach, for example, 132° C. for several minutes in a pre-vacuum sterilizer or 121° C. for 30 minutes or longer in a gravity displacement sterilizer.

Like the surgical tools and instruments, the battery enclosures of such tools are also sterilized. This sterilization presents a problem as the performance of rechargeable battery cells can be degraded if they are exposed to temperatures in excess of 70° C. Beyond degraded performance, the battery cells themselves are at risk of being permanently damaged upon exposure to temperatures in excess of 80° C.

One approach to prevent the battery cells from reaching such critical temperatures has been to sterilize the battery enclosure without the battery cells. The battery cells are then added to the enclosure with the use of shields and sealable covers to prevent exposure of the cells to the sterile field. Another approach has been to insulate the battery cell with the use of insulation materials, such as microporous silicate (U.S. Pat. No. 6,756,766) or silica (silicon dioxide) or silica ceramic carbon nitride and silica aerogel (U.S. Pat. No. 8,486,560).

Yet another approach has been to use chemicals and gasses to sterilize the battery enclosure with the battery cells. This type of sterilization process avoids generating temperatures that could potentially damage the battery cells. However, this approach requires sterilization infrastructure not typically present in hospitals, surgery centers and other healthcare institutions.

SUMMARY

A simple low cost, sealed battery enclosure and associated method of manufacture is provided. In the exemplary embodiment, the enclosure can be autoclaved with the rechargeable battery (electrochemical) cells enclosed therein.

According to one aspect of the exemplary embodiment, a battery pack assembly comprises at least one battery comprising an electrochemical cell and an enclosure having at least an outer wall configured to create a sealed volume of space substantially around the at least one battery. An atmosphere of the volume of space comprises gas. The thermal conductivity of the gas in the volume of space is less than 0.018 watts per meter per degree Celsius.

DETAILED DESCRIPTION

The exemplary embodiments described herein are provided for illustrative purposes only and are not limiting of the scope of the invention. It is understood that various omissions and substitutions of equivalent structures are contemplated as circumstances may suggest or render expedient as known to one of skill in the art. Furthermore, although the following relates substantially to exemplary embodiments of the physical design, it will be understood by those familiar with the art that changes to materials, part descriptions and geometries can be made without departing from the spirit of the invention.

In one aspect of an exemplary embodiment of the invention, a battery pack assembly or enclosure comprises one or more batteries having an electrochemical cell and an enclosure having at least an outer wall configured to create a sealed volume of space substantially around the batteries. An atmosphere of the volume of space comprises gas having a thermal conductivity less than 0.018 watts per meter per degree Celsius. This atmosphere of gas provides an insulative layer between the outer wall of the enclosure and the batteries. With this insulative layer, the battery pack assembly can be subjected to autoclaving without damaging the batteries.

The thermal conductivity of the gas in the volume of space can be lower, such as less than 0.016 watts per meter per degree Celsius. In addition, the atmosphere of the volume of space can include a partial vacuum sufficient to make the thermal conductivity of the gas in the volume of space less than 0.018 watts per meter per degree Celsius. The gas included in the atmosphere of the volume of space can be at least 25% or at least 33% of an inert gas selected from the group consisting of krypton, xenon, argon, and freon.

The battery pack assembly can also include a plurality of standoffs that separate the batteries from the outer wall of the enclosure. In addition, an inner wall can be included that at least partially encloses the batteries. The outer wall of the enclosure is formed from a composite plastic that can be covered with a coating such as a metallization layer that reduces the permeation rate of the outer wall.

To provide power, the battery pack assembly includes battery terminals that extend from the batteries to the exterior of the outer wall. The battery terminals include a positive terminal and a negative terminal that are coupled to electrical contacts, which are configured to connect to and power a surgical tool as well as to connect to and be charged by a recharging station.

Figure 1:
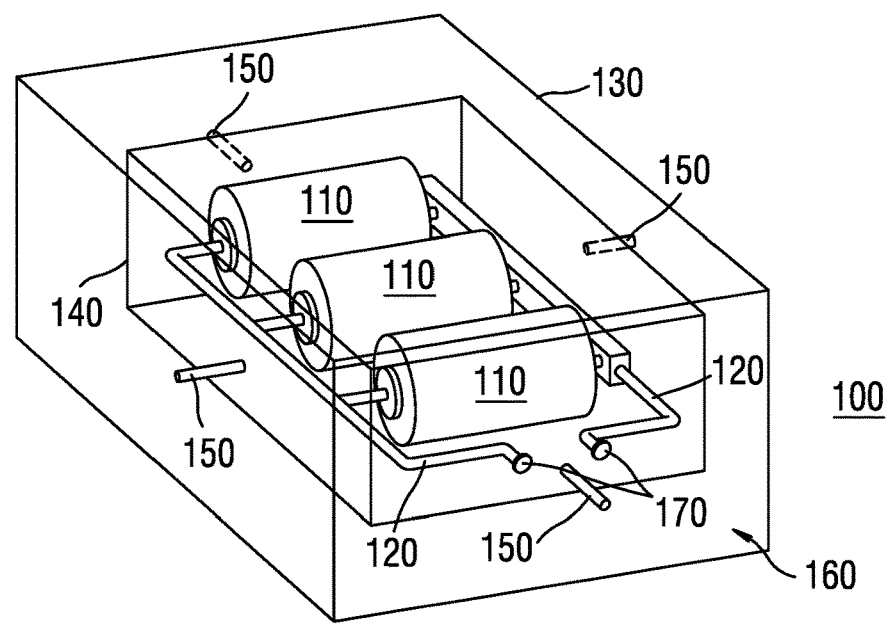
FIG. 1 is an illustration of a perspective view of a battery pack assembly consistent with an aspect of an exemplary embodiment of the invention.

As shown in FIG. 1, a battery pack enclosure or assembly 100 includes battery cells 110, battery terminals 120, a first or outer wall 130, and a second or inner wall 140. The battery cells 110 can be rechargeable, electrochemical batteries, such as lead-acid, nickel cadmium (NiCd), nickel metal hydride (NiMH), lithium ion (Li-ion), or lithium ion polymer (Li-ion polymer).

The outer wall 130 forms a contiguous, sealed compartment around the inner wall 140 and the battery cells 110. The space between an interior surface of the outer wall 130 and an exterior surface of the inner wall 140 represents a volume of space 160 having an atmosphere comprising gas, a partial vacuum, or both. The inner wall 140 can be a contiguous or non-contiguous wall around the battery cells 110. When implemented as a non-contiguous wall, the inner wall 140 can partially or substantially cover the battery cells 110 and separate them from the interior surface of the outer wall 130. The inner wall 140 preferably has a cross-sectional area that is less than 25% of the exterior area of the outer wall 130. Reducing the cross-sectional area of the inner wall 140 with respect to the outer wall 130 helps to minimize conductive heat transfer through the battery pack enclosure 100 from the outer wall 130 to the battery cells 110.

Figure 2:
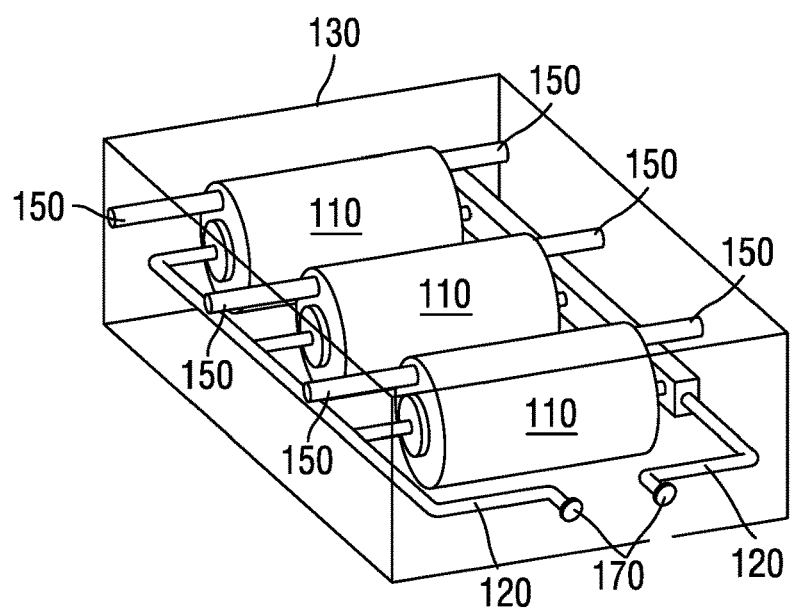
FIG. 2 is an illustration of a perspective view of a battery pack assembly consistent with another aspect of an exemplary embodiment of the invention.

To separate the outer wall 130 from the inner wall 140, the battery pack enclosure 100 includes a plurality of standoffs, spacing material or separators 150 that maintain the separation of the outer wall 130 from the inner wall 140. In the exemplary embodiment the spacing material is formed of individual standoffs 150 that prevent the battery cells 110 from contacting the outer wall 130. Of course, alternative arrangements are contemplated that provide a filler, or contiguous spacing rather than discrete structural "standoffs." Alternatively, as shown in FIG. 2, the battery pack enclosure 100 can be designed without the inner wall 140. In this configuration, the battery cells 110 are exposed to the atmosphere in the volume of space 160. Without the inner wall 140, the standoffs 150 are arranged to separate the outer wall 130 from the battery cells 110, as shown in FIG. 2.

The standoffs 150 are preferably formed from a material having a low thermal conductivity material, which helps to reduce heat transfer from the outer wall 130 to the inner wall 140 and the battery cells 110. In addition, the cross-sectional area of the standoffs 150 is preferably minimized. For example, the cross-sectional area can be a fraction of the surface area of the battery cells 110, such as less than 10%. The number of standoffs 150 included within the battery pack enclosure 100 depends on the particular configuration of the battery cells 110, but the number of standoffs 150 is preferably a number sufficient to maintain the position of the battery cells 110 (or inner wall 140 if included) within and away from the outer wall 130.

Whereas the exterior surface of the outer wall 130 is exposed to the environment, the interior surface of the outer wall 130 is exposed to the atmosphere in the volume of space 160 between the outer wall 130 and the inner wall 140 or battery cells 110. This atmosphere provides an insulative layer between the outer wall 130 and the battery cells 110. The atmosphere of gas can comprise, for example, at least 25% of a low thermal conductivity gas. The low thermal conductivity gas can comprise larger portions of the atmosphere, such as at least 33%, at least 50%, or all of the atmosphere in the volume of space 160. The low thermal conductivity gas is preferably an inert gas such as Argon, Krypton, Xenon, or Freon.

In addition to the low thermal conductivity gas, or as an alternative to the low thermal conductivity gas, the atmosphere in the volume of space 160 can comprise a partial vacuum. The partial vacuum preferably amounts to at least 25% of the atmosphere in the volume of space 160. The partial vacuum can comprise larger portions of the atmosphere, such as at least 33%, at least 50%, or all of the atmosphere in the volume of space 160.

The partial vacuum helps to reduce heat transfer from the outer wall 130 to the battery cells 110 because heat transfer at atmospheric pressure is predominantly affected by either direct transfer during gas molecule-to-molecule collisions or by molecular motion convection. If two objects, such as the outer wall 130 and the battery cells 110, are at different temperatures and placed in a chamber at atmospheric pressure, heat will begin to flow from the hotter to the colder through the gas molecules. If such pressure is reduced by removing some of the gas molecules, such as by introducing a partial vacuum, the distance between the molecules will become greater and the number of molecular collisions will become decrease, thereby resulting in a reduction of heat flow. Lowering the thermal conductivity of the heat transfer medium (such as the gas molecules) permits the hotter object to retain its heat. Moreover, if the pressure is continually reduced, the heat flow will similarly be continually reduced. Thus, introducing at least a partial vacuum between the hot and cold objects (e.g., the outer wall 130 and the battery cells 110) creates a thermal insulator. The amount of insulation provided by the partial vacuum depends on the amount of the vacuum (i.e., the paucity of molecules) between the hot and cold objects.

Whether the atmosphere in the volume of space 160 comprises a low thermal conductivity gas, a partial vacuum, or a combination of them, the thermal conductivity for the atmosphere is preferably configured to insulate the battery cells sufficiently to protect the battery cells 110 from being damaged during an autoclave cycle. The thermal conductivity of air is 0.024 watts per meter degree Celsius. Using the low thermal conductivity gas and/or partial vacuum reduces the thermal conductivity of the atmosphere in the volume of gas 160 to be lower than the thermal conductivity of air. To provide protection to the battery cells 110, sufficient low thermal conductivity gas and/or partial vacuum is preferably provided in the atmosphere to make the range of thermal conductivity for the atmosphere, for example, from 0.002 to 0.018 watts per meter degree Celsius. More preferably, the thermal conductivity of the atmosphere is less than 0.018, less than 0.016, less than 0.012, less than 0.009, or less than 0.007 watts per meter per degree Celsius. In an exemplary embodiment, the low thermal conductivity gas has a thermal conductivity of less than 0.012 watts per meter degree Celsius such as Freon (having a thermal conductivity of 0.007) or Krypton (having a thermal conductivity of 0.009.) With the atmosphere of the volume of space 160 configured to have a low thermal conductivity, the battery pack enclosure 100 prevents, for example, the inner wall 130 and the battery cells 120 from reaching 70° C. when the outer wall is exposed to 132° C. for four minutes or 121° C. for 30 minutes.

To provide further protection of the battery cells 110 beyond the insulative layer provided by the atmosphere in the volume of space 160, the walls of the battery pack enclosure 100 can comprise a material having a very low permeation rate to gases including Nitrogen, Oxygen and any other gas present in the atmosphere. The material preferably has a very low permeation rate both at room temperature as well as at autoclave temperatures, such as 132° Celsius. The material for the outer wall 130 and inner wall 140 can be, for example, a composite plastic having different webs and layers to reduce permeability. The thickness of the outer wall 130 is preferably sufficient to withstand damage, such as from being dropped on a floor, as well as to account for the impact and molding characteristics of the material used, such as plastic.

In addition to the material for the walls of the battery pack enclosure 100, a membrane, coating, co-extrusion or plating can be provided on the interior or exterior of the outer wall 130, and optionally to the inner wall 140 as well. The coating is preferably located at least on the interior of the outer wall 130 to protect from damage, such as from scratching. The coating, which can be a metallization layer for example, helps to decrease the permeation rate of the walls, preferably by at least 90%. The desired low permeation rate will generally be a function of the "free gas volume" inside the outer wall 130 of the battery pack enclosure 100. In a preferred embodiment, for example, the material of the outer wall 130 and the coating are preferably designed to permit a transfer of no more than 10% of the free volume within the atmosphere of the volume of space 160 within one year when stored at 23° C. With such a low permeation rate, the atmosphere within the volume of space 160 does not dissipate from the battery pack enclosure 100 over time.

Figure 3:
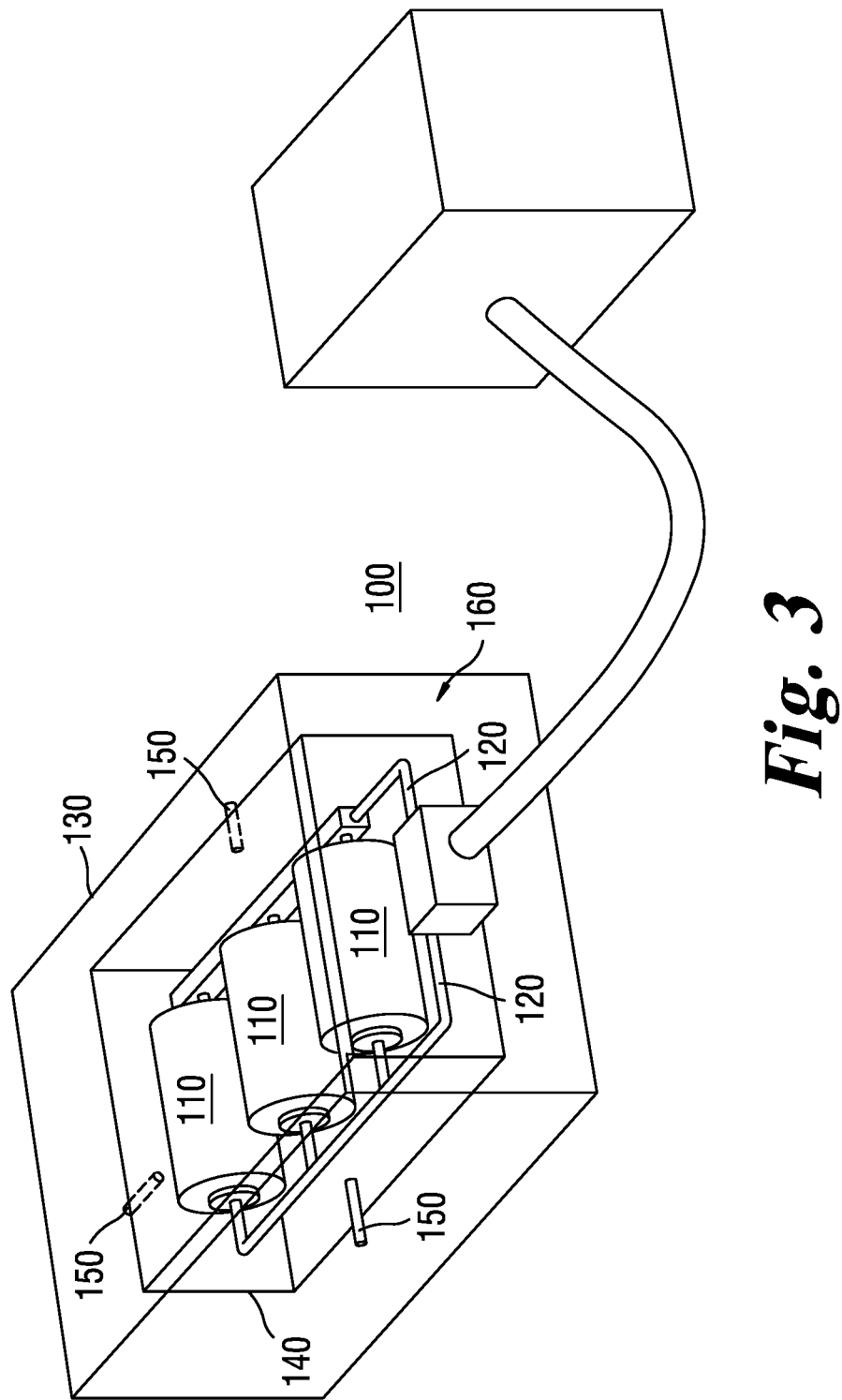
FIG. 3 is an illustration of a perspective view of a battery pack assembly coupled to a recharging station consistent with an aspect of an exemplary embodiment of the invention.
Figure 4:
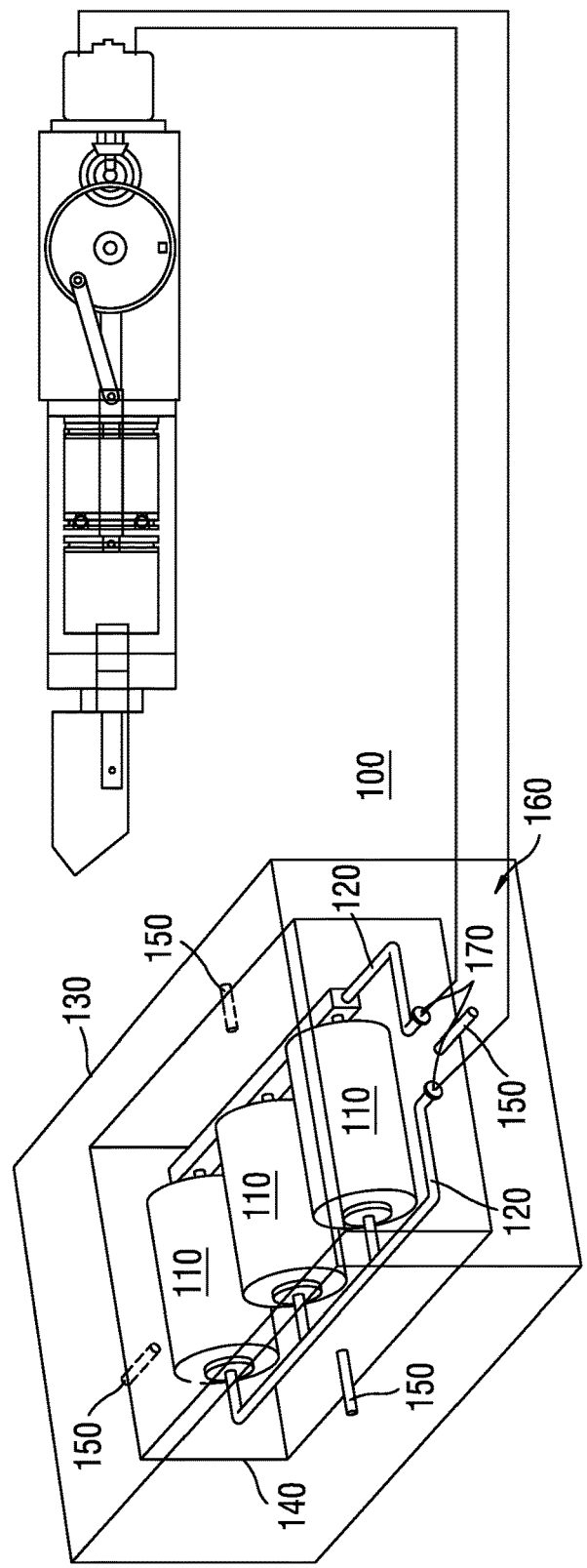
FIG. 4 is an illustration of a perspective view of a battery pack assembly coupled to a surgical device consistent with an aspect of an exemplary embodiment of the invention.

The battery terminals 120 can include positive and negative leads that can connect to electrical contacts 170. The electrical contacts 170 are configured to connect and provide power to a device such as a surgical tool, such as shown in FIG. 4. The surgical tool can be, for example, an orthopedic power tool such as the one described in U.S. Pat. No. 8,936,106. The electrical contacts 170 can also connect to a battery charger to recharge the battery cells 110, such as shown in FIG. 3. The battery terminals 120, which pass through the outer wall 130 and the inner wall 140, are preferably sealed by a low permeability potting compound, O-ring or other sealing method to minimize gas leakage. The sealing material can be, for example, 20-2350 polyurethane. Additionally, the cross-sectional area of the electrical contacts 170 is kept at a minimum in order to reduce conductive heat transfer to the battery cells 110.

Figure 5:
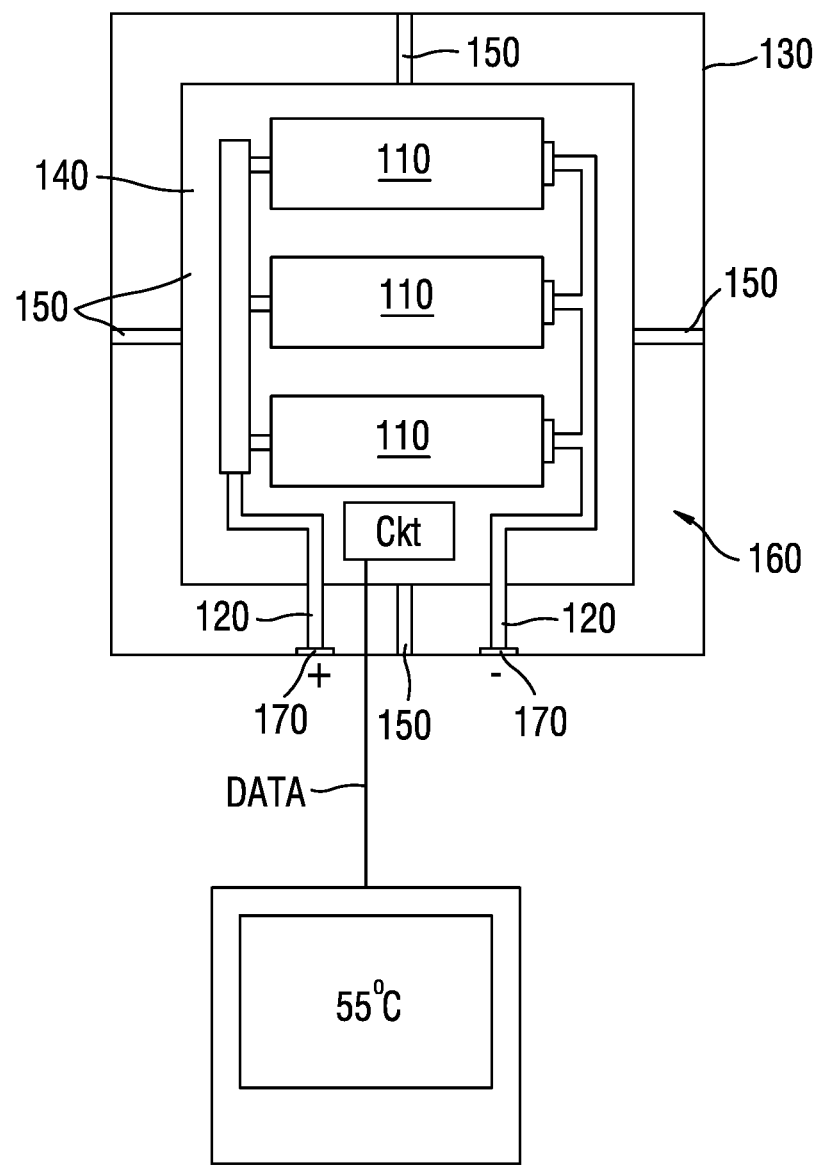
FIG. 5 is an illustration of a perspective view of a battery pack assembly including a display consistent with an aspect of an exemplary embodiment of the invention.

In addition to the positive and negative leads, the battery terminals 120 can also include one or more communication terminals. These communication terminals can be configured to provide information about breaches of the atmosphere, the temperature of the battery cells 110, the charge level of the battery cells, and any other information relevant to the operation or condition of the battery pack enclosure 100 including the battery cells 110. To provide this information via the communication terminals, the battery pack enclosure 100 can include circuitry, detectors, and transducers configured to detect the conditions and parameters related to the operation of the battery pack enclosure 100 and the battery cells 110. The communication terminals can be coupled to a display 180, such as shown in FIG. 5, which is configured to display information provided by the communication terminals. A fuel cell may also be substituted for the electro-chemical battery cell.

To detect temperature, the batter pack enclosure 100 can include a thermal couple that monitors the temperature of the battery cells 1120 or the area around the battery cells 110. Indicator lights visible on the exterior surface of the outer wall 130 or sounds from a speaker mounted on the exterior surface of the outer wall may be used to indicate the status of the temperature, such as if the temperature remains at an acceptable level, has reached a point approaching critical level, or has reached a critical level. The indicator lights and sound can also be used to indicate whether a battery is ready to be used or not. A thermochromic strip can also be provided that indicates via color or other change that the battery cells 110 are at a safe operating temperature.

Besides detecting and providing indications of temperature, the battery pack enclosure 100 can include a failsafe that, when activated, prevents the battery from being used. The failsafe can be implemented, for example, by blowing a fuse in the connection. Additional safeties commonly used in the industry, such as PTC elements, may be incorporated in the battery pack enclosure 100 to prevent the battery cells 110 from being discharged until they have cooled sufficiently. The battery pack enclosure 100 can also include a sensor for detecting the thermal conductivity of the internal gas chamber area and a sensor for detecting the peak temperature reached by the battery cells 110 within the battery pack enclosure 100 during an autoclave cycle. Based on the detected information, the sensors can communicate information to an operator, such as a breach in the thermal insulation system or a defect with the battery cells 110, e.g., that the battery cells 110 will not charge.

Although there have been described particular embodiments of the present disclosure, it is not intended that such references be construed as limitations on the scope of the disclosure.

What is claimed is:

1. A battery pack assembly comprising:
at least one battery comprising an electrochemical cell;
a communication interface;
an enclosure having at least an outer wall configured to create a sealed volume of space; and
a sensor for detecting thermal information indicative of a breach of the battery pack assembly, the thermal information provided to the communication interface based on a detected condition within the sealed volume of space; wherein an atmosphere of the volume of space comprises gas, a thermal conductivity of the gas in the volume of space is less than 0.018 watts per meter per degree Celsius, the sealed volume of space encompasses an inner surface of the outer wall to a region substantially around the at least one battery, and the sensor is a thermal conductivity sensor.

2. The battery pack assembly of claim 1, wherein the thermal conductivity of the gas in the volume of space is less than 0.016 watts per meter per degree Celsius.

3. The battery pack assembly of claim 1, wherein an atmosphere of the volume of space includes a partial vacuum sufficient to make the thermal conductivity of the gas in the volume of space less than 0.018 watts per meter per degree Celsius.

4. The battery pack assembly of claim 1, wherein an atmosphere of the volume of space includes at least 25% of an inert gas selected from the group consisting of krypton, xenon, argon, and freon.

5. The battery pack assembly of claim 1, wherein an atmosphere of the volume of space includes at least 33% of an inert gas selected from the group consisting of krypton, xenon, argon, and freon.

6. The battery pack assembly of claim 1, further comprising a plurality of standoffs that separate the at least one battery from the outer wall of the enclosure.

7. The battery pack assembly of claim 6, wherein the enclosure further comprises an inner wall at least partially enclosing the at least one battery, wherein the plurality of standoffs separate the inner wall from the outer wall.

8. The battery pack assembly of claim 1, wherein the outer wall of the enclosure is formed from a composite plastic.

9. The battery pack assembly of claim 8, wherein at least one of an exterior surface and an interior surface of the outer wall of the enclosure includes a coating that reduces the permeation rate of the outer wall.

10. The battery pack assembly of claim 9, wherein the coating includes a metallization layer.

11. The battery pack assembly of claim 1, further comprising battery terminals, wherein the battery terminals extend from the at least one battery to the exterior of the outer wall.

12. The battery pack assembly of claim 11, wherein the battery terminals comprise a positive terminal and a negative terminal.

13. The battery pack assembly of claim 12, further comprising a second sensor that detects a peak temperature reached by the at least one battery during an autoclave cycle, wherein the second sensor provides information via the communication terminal of the detected peak temperature.

14. The battery pack assembly of claim 12, further comprising electrical contacts coupled to the positive terminal and the negative terminal.

15. The battery pack assembly of claim 14, wherein the electrical contacts are configured to connect to a recharging station.

16. The battery pack assembly of claim 1, wherein the communication interface provides information regarding the temperature of the at least one battery.

17. The battery pack assembly of claim 1, wherein a temperature of the at least one battery remains below 70° C. when the outer wall is exposed to 132° C. for four minutes.

18. The battery pack assembly of claim 1, wherein a temperature of the at least one battery remains below 70° C. when the outer wall is exposed to 121° C. for 30 minutes.

19. A surgical tool comprising:
a battery pack assembly to provide power to the surgical tool, having at least one battery comprising an electrochemical cell,
a communication terminal,
a sensor for detecting thermal information indicative of a breach of the battery pack assembly, and
an enclosure comprising at least an outer wall configured to create a sealed volume of space that extends from an inner surface of the outer wall to a region substantially around the at least one battery, the communication terminal, and the sensor;
wherein the sensor is a thermal conductivity sensor and provides the thermal information indicative of the breach of the battery pack assembly via the communication terminal based on a detected condition within the sealed volume of space; and wherein an atmosphere of the volume of space comprises gas, wherein the a thermal conductivity of the gas in the volume of space is less than 0.018 watts per meter per degree Celsius.

* * * * *